United States Patent

Mizutani

Patent Number: 5,851,204
Date of Patent: Dec. 22, 1998

[54] DISPOSABLE ABSORBENT ARTICLE

[75] Inventor: Satoshi Mizutani, Kawanoe, Japan

[73] Assignee: Uni-Charm Corporation, Ehime-ken, Japan

[21] Appl. No.: 747,706

[22] Filed: Nov. 12, 1996

Related U.S. Application Data

[63] Continuation of Ser. No. 437,744, May 9, 1995, abandoned.

[30] Foreign Application Priority Data

May 10, 1994 [JP] Japan .................................. 6-096600

[51] Int. Cl.⁶ ...................................................... A61F 13/15
[52] U.S. Cl. .................................... 604/385.2; 604/385.1; 604/358; 604/378; 604/387; 604/383
[58] Field of Search .................................... 604/358, 370, 604/378, 385.1, 383, 385.2, 386, 387, 397, 398

[56] References Cited

U.S. PATENT DOCUMENTS

| | | |
|---|---|---|
| 2,939,461 | 6/1960 | Joa . |
| 5,019,067 | 5/1991 | Simmons . |
| 5,026,364 | 6/1991 | Robertson ............................ 604/385.1 |
| 5,064,421 | 11/1991 | Tracy . |
| 5,085,654 | 2/1992 | Buell .................................... 604/385.2 |
| 5,308,346 | 5/1994 | Sneller et al. ........................ 604/385.2 |
| 5,330,461 | 7/1994 | Leeker ................................. 604/385.1 |
| 5,342,342 | 8/1994 | Kitaoka ................................ 604/385.2 |
| 5,704,928 | 1/1998 | Morita et al. ............................ 604/387 |

FOREIGN PATENT DOCUMENTS

| | | |
|---|---|---|
| 0 319 314 | 6/1989 | European Pat. Off. . |
| 0 534 488 A1 | 3/1993 | European Pat. Off. . |
| 2 259 441 | 3/1993 | United Kingdom . |

*Primary Examiner*—Paul B. Prebilic
*Assistant Examiner*—Francis K. Cuddihy
*Attorney, Agent, or Firm*—Lowe Hauptman Gopstein Gilman & Berner

[57] ABSTRACT

A disposable absorbent article, such as a menstruation pad or diaper, is provided with a pair of side flaps extending along transversely opposite side edges of a liquid-absorbent core disposed between a liquid permeable topsheet and a liquid impermeable backsheet. Each longitudinally extending side flap is made from a soft, stretchable and liquid-resistant strip of sheet material. One of the transversely opposite sides of the strip is bonded to the topsheet while the other side is bonded to the backsheet.

5 Claims, 4 Drawing Sheets

DISPOSABLE ABSORBENT ARTICLE

This application is a continuation of application Ser. No. 08/437,744 filed May 9, 1995 now abandoned.

BACKGROUND OF THE INVENTION

The present invention relates to disposable absorbent articles such as menstruation pads, diapers, training pants, incontinent pants and pads.

There are well known disposable absorbent articles comprising a liquid-permeable topsheet, a liquid-impermeable backsheet, a liquid-absorbent core disposed between these two sheets and a pair of side flaps extending outward beyond transversely opposite side edges of the absorbent core, respectively. The top- and backsheets are made of sheet materials, for example, a nonwoven fabric and/or a plastic film. These top- and backsheets are bonded to each other in their areas extending outward beyond the transversely opposite side edges of the absorbent core to form the side flaps. The side flaps not only provide a zone over which the top- and backsheets are bonded to each other but also fit around the wearer's legs to prevent body fluids from sideways leaking. In the case of a menstruation pad, they cover the shorts (pants) worn by the wearer of the pad along transversely opposite side edges of its crotch zone and thereby protect the side edges of the shorts against being smeared with menstrual discharge.

However, the side flaps and the outer edges thereof formed in the manner as described above are nothing but the portions of the top- and backsheets bonded together and their cut ends, respectively. Accordingly, even if both the top- and backsheets themselves are of soft materials, once they have been bonded together, the side flaps formed by these soft sheets may have a relatively high rigidity and give the wearer's soft skin particularly over the crotch zone and therearound an uncomfortable feeling. Specifically, the outer edges of the respective side flaps defined by the cut ends of the top- and backsheets bonded together may unbearably irritate the wearer's skin like sharp edges.

Accordingly, it is a principal object of the invention to form each of the side flaps by folding a strip of soft, stretchable and liquid-resistant sheet material on itself substantially along its transversely intermediate line so as to cover each of the transversely opposite side edges of the article, bonding the one of its transversely opposite sides to the topsheet, then bonding the other side opposed to said one side to the backsheet with the fold defining the outer side edge of this flap, and thereby to solve the above-mentioned problem.

SUMMARY OF THE INVENTION

The object set forth above is achieved, according to the invention, by a disposable article comprising a liquid-permeable topsheet, a liquid-impermeable backsheet, a liquid-absorbent core disposed between these two sheets, and a pair of side flaps extending outwardly beyond transversely opposite side edges of said core, wherein each of said side flaps is formed by bonding a strip of soft, stretchable and liquid-resistant sheet material to said topsheet on its upper surface along one of transversely opposite sides of said strip, folding a portion of said strip extending outward beyond the associated side edge of said core along a transversely intermediate line of said portion back onto said backsheet and bonding the other side of said strip opposed to said one side bonded to said topsheet to said backsheet.

According to a preferred embodiment of the invention, bonding of the strips to the article is performed in a stretched condition of the strips along the side edges of the core to facilitate close contact of the article with the wearer's body.

With the absorbent article as described above, each side flap comprises the soft, stretchable and liquid-resistant strip folded back along the transversely intermediate line of the strip's portion outwardly extending beyond the topsheet with the fold defining the outer side edge of the side flap, so there is no apprehension that the outer side edge might irritate the wearer's skin. The side flaps are bonded with a longitudinal tension to the article in order to assure that the article may be appropriately curved and put closely against the wearer's skin over the crotch as well as therearound under the effect of the side flaps' contraction occurring as the article is worn.

PREFERRED EMBODIMENT OF THE INVENTION

Figure 1:
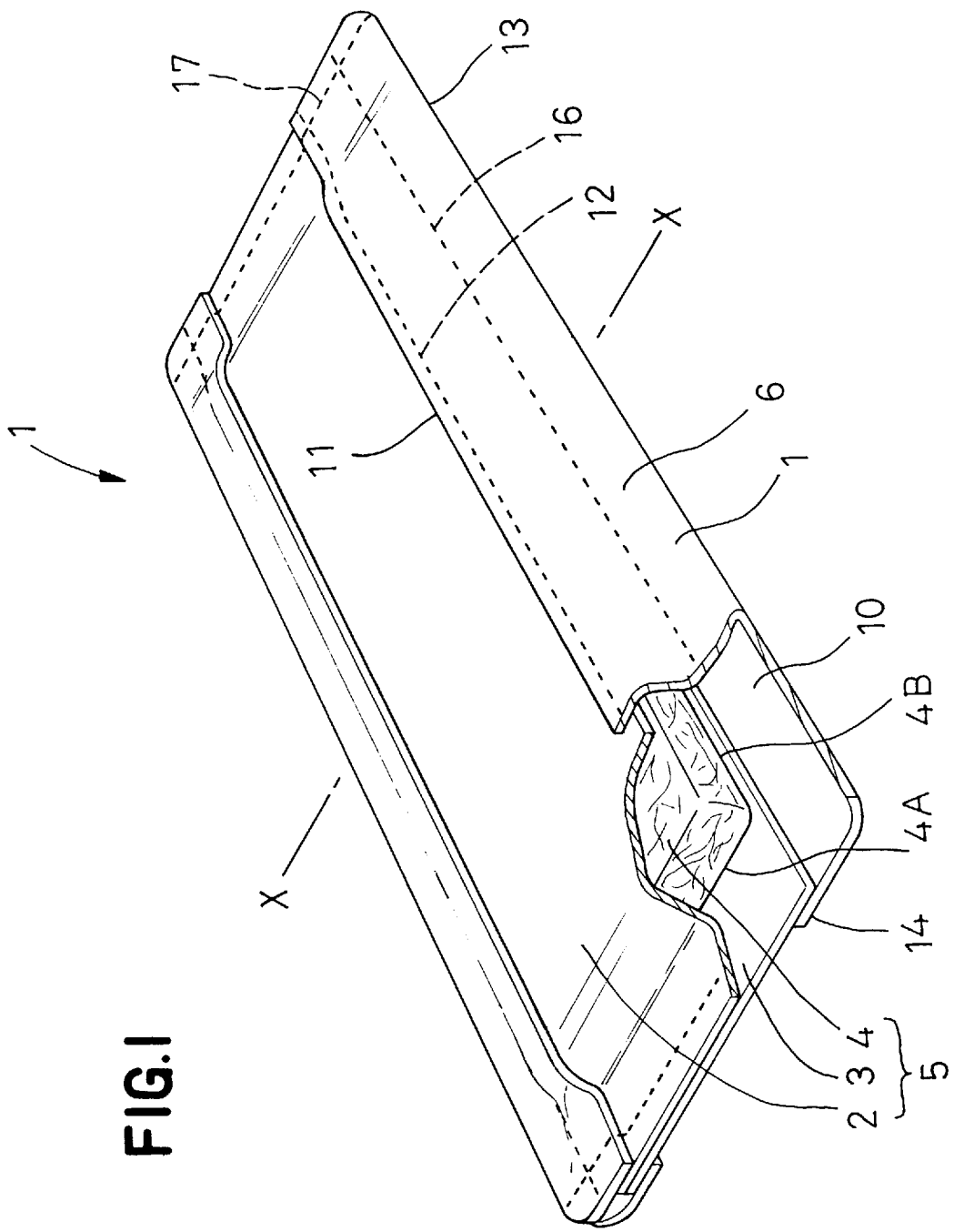
FIG. 1 is a perspective view showing a menstruation pad as a disposable absorbent article of the invention partially broken away.
Figure 2:
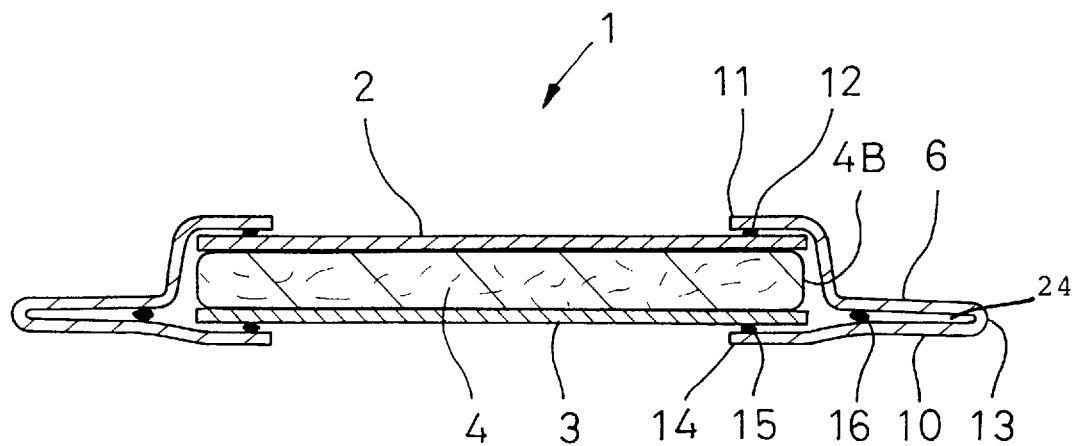
FIG. 2 is a sectional view taken along a line X—X in FIG. 1.

Referring to FIGS. 1 and 2, a menstruation pad 1 comprises a longitudinally long basic body 5 including a liquid-permeable topsheet 2, a liquid-impermeable backsheet 3 and a liquid-absorbent core 4 disposed between these two sheets 2, 3, and a pair of side flaps 6 on both sides of the basic body 5. The top- and backsheets 2, 3 are water-tightly bonded to each other in their end portions extending outward beyond longitudinally opposite ends 4A of the core 4, on one hand, and bonded, in the proximity of transversely opposite side edges 4B of the core 4, to longitudinal long strips 10 of a soft, stretchable and liquid-resistant sheet material, respectively which are destined to form the side flaps 6, on the other hand. Each of the strips 10 forms the side flaps such that longitudinal one side of the strip 10 is bonded along a longitudinally continuous welding line 12 to the upper surface of the topsheet 2, a portion of strip 10 extending outward beyond longitudinally side edge 4B is folded along a transversely intermediate line 13 back onto the backsheet 3, the other longitudinal side 14 thereof is bonded to the lower surface of the backsheet 3 along a longitudinally continuous welding line 15. Mutually opposed inner surfaces of each side flap 6 are bonded to each other along a longitudinally continuous or intermittent welding line 16 extending in parallel to the associated side edge 4B of the core 4 between the side edge 4B and said folding line 13, in other words, apart inward from an outer side edge of each side flap 6 so that they may define a tunnel 24 having a pump function to flow air therethrough between the lines 13 and 16 when the tunnel is pushed against the wearer's skin.

The strip 10 may be of stretchable material such as a stretchable nonwoven fabric obtained by crimping composite fibers, a melt-blown nonwoven fabric made from stretchable fibers, or a stretchable sheet of elastomer or rubber. When fibrous materials are employed, their fineness are preferably less than 5 deniers and more preferably less than 2 deniers. The strip 10 preferably has a weight per unit area less than 100 g/m² and more preferably less than 50 g/m² to obtain desired softness as well as stretchability. It is required for such strip 10 to have an ability of limiting or preventing the body fluids from soaking in the direction of its thickness or spreading therethrough in its planar direction, i.e., a water-proofness. The strip 10 may be subjected to a water repellent finish or the like, if desired. Bonding between the mutually opposed inner surfaces of the strip 10 as well as between the strip 10 and the top- and backsheets 2, 3 should be of water-impervious nature and, to achieve this, it is preferable to provide at least the welding lines 11, 15 in the form of longitudinally continuous lines. It should be understood that the welding lines 11, 15, 16 can be effectively employed only when the top- and backsheets 2, 3 as well as the strip 10 are of fusible nature, so these welding lines may be replaced by the corresponding lines of hot melt adhesive or the like, if necessary. To avoid leakage of the body fluids possibly occurring along the longitudinally opposite ends of each side flap 6, the strips 10 should be bonded to the backsheet 3. In this manner, the body fluids may spread through the topsheet 2 in its planar direction but never spread over the upper surfaces of the respective strips 10.

Figure 3:
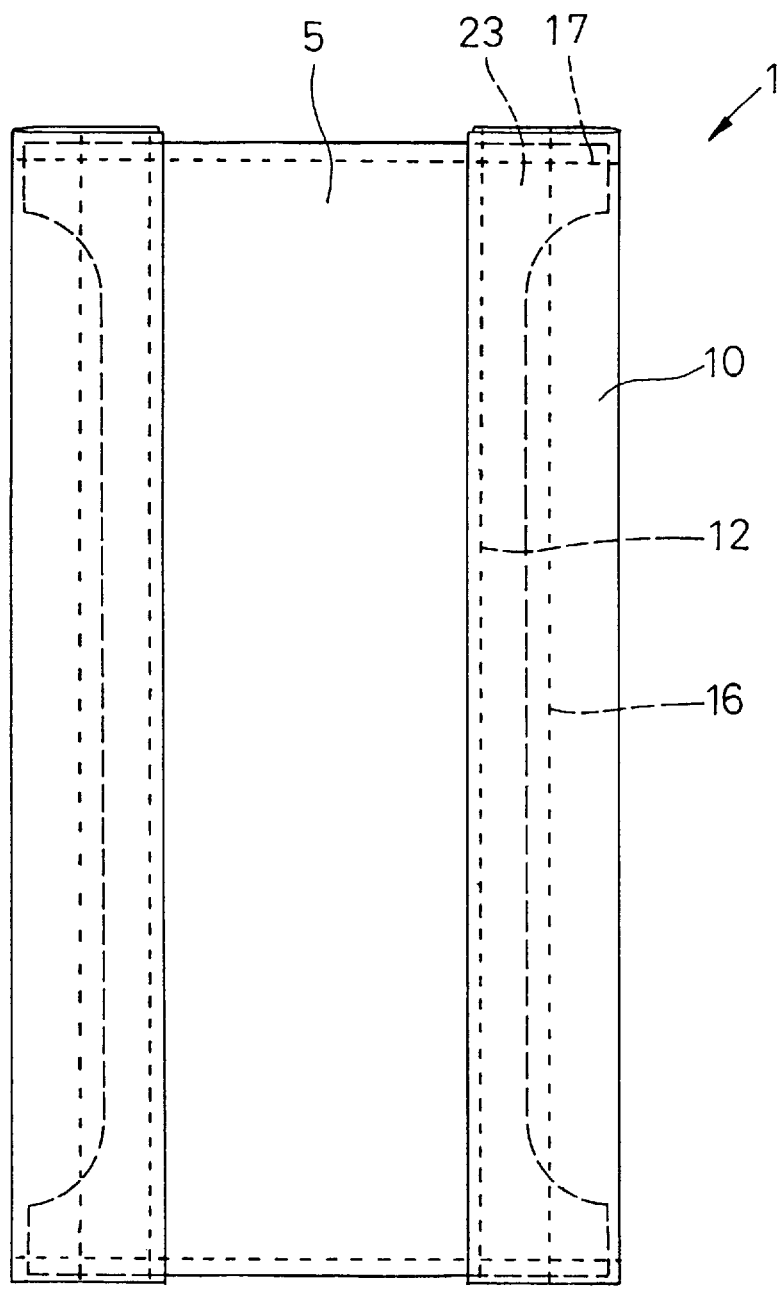
FIG. 3 is a plan view showing a variant of the menstruation pad shown by FIG. 1.

Referring to FIG. 3 showing another embodiment of the pad 1, each of the longitudinally opposite ends of the basic body 5 partially extends outward in transversely opposite directions so as to form lugs 23. Each strip 10 covers each pair of the longitudinally opposite lugs 23 on their upper and lower surfaces. In this state, the strip 10 is bonded to the top- and backsheets 2, 3 along bonding lines 12, 15 (the bonding line 15 is not shown in FIG. 3, see FIG. 2), respectively, and then the mutually opposed inner surfaces of this strip 10 are bonded to each other along a bonding line 16. The strip 10 is also bonded along a bonding line 17 to the respective sections of the top- and backsheets 2, 3 which define the lugs 23. With such an arrangement of the pad 1, the side flap 6 formed is stretchable between the pair of transversal bonding lines 17 provided along the longitudinally opposite ends of the pad 1.

According to the embodiment of the pad 1 shown by FIGS. 1 and 3, the strips 10 may be bonded with a longitudinal tension to the basic body 5 to form the side flaps 6 and thereby it is facilitated to put the pad 1 closely against the wearer's crotch, since the topsheet 2 is inwardly curved under the contraction of the side flaps 6 as the pad 1 is worn. The arrangement of the pad 1 shown by FIG. 3 is particularly preferable to achieve this effect. According to the arrangement of the pad 1 shown by FIGS. 1 and 3, the side flaps 6 are soft and have a relatively low rigidity while the basic body 5 has a relatively high rigidity due to the presence of the core 4 therein. Such feature is advantageous in that, even when the side flaps 6 are creased as the pad 1 is worn, these creases neither extend into the basic body 5 nor cause the basic body 5 to be creased and an apprehension is eliminated that a desired fitness of the pad 1 against the wearer's crotch might be affected thereby.

Figure 5:
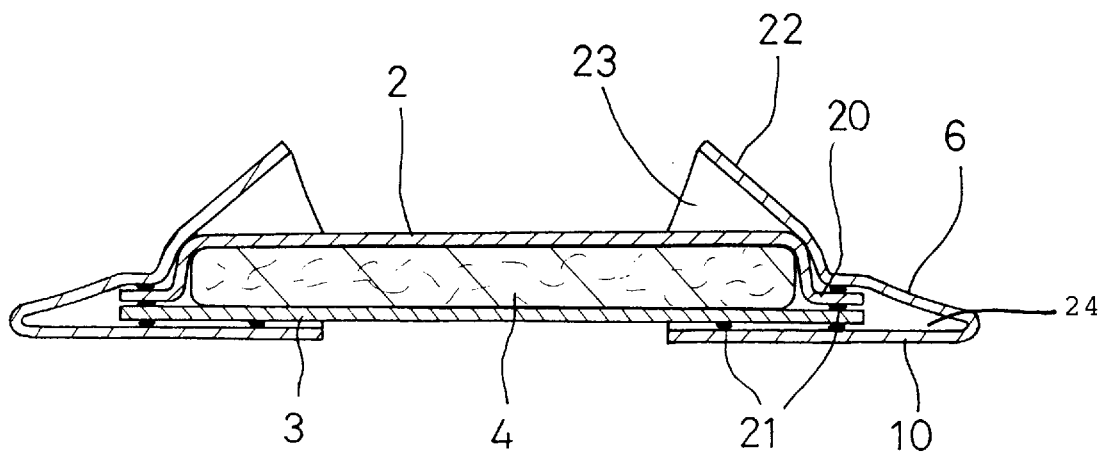
FIG. 5 is a sectional view taken along a line Y—Y in FIG. 4.
Figure 4:
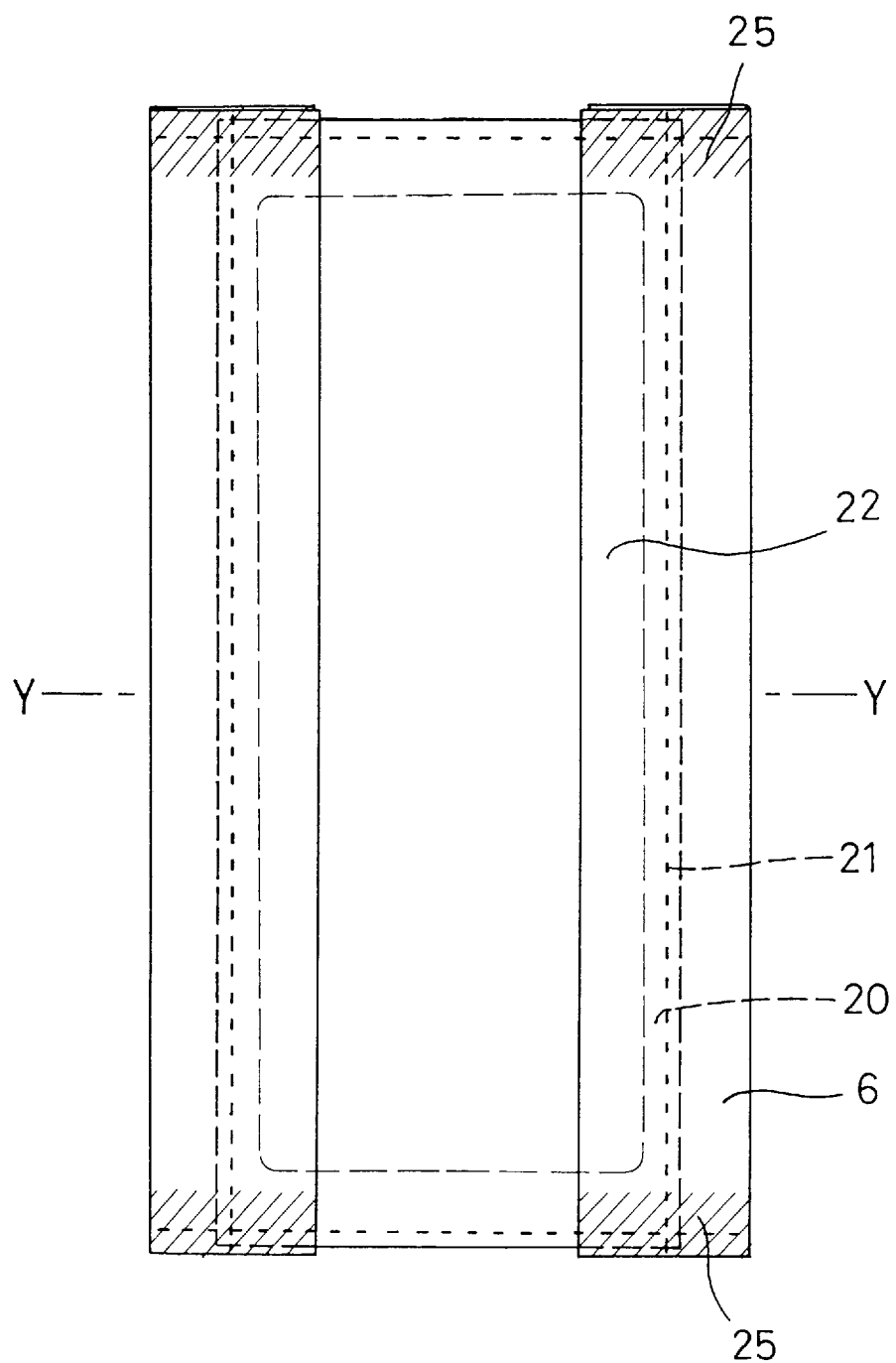
FIG. 4 is a view similar to FIG. 3 but showing another variant of the menstruation pad shown by FIG. 1.

Referring to FIGS. 4 and 5 showing still another embodiment of the pad 1, the top- and backsheets 2, 3 extend outward slightly beyond the transversely opposite side edges of the liquid-absorbent core 4 to form relatively narrow side flaps 20 and thereon the strips 10 are bonded to the top- and backsheets 2, 3 along longitudinal welding lines 21, respectively, to form the side flaps 6 extending outward from the respective welding lines 21 as well as side flaps 22 extending inward from the respective welding lines 21 to above the core 4 so that the respective side flaps 22 may cooperate with the topsheet 2 to form pockets which are openable inwardly of the pad 1. Referring to FIG. 4, in areas of each strip 10 shaded by oblique lines 25, each strip 10 has its mutually opposed inner surfaces bonded to each other and to the upper surface of the topsheet 2 or to the lower surface of the backsheet 3. So far as the first side flaps 6 are concerned, the mutually opposed inner surfaces of each strip 10 may be bonded to each other or left in freely overlying relationship. According to the arrangement of FIGS. 4 and 5, the strips 10 may be bonded with a longitudinal tension to the basic body 5 in order to assure that the side flaps 22 tend to rise on the topsheet 2 under the effect of their elastic contraction as the pad 1 is worn. As a result, the pockets 23 are opened as shown by FIG. 5.

As will be apparent from the foregoing description, each side flap (more strictly, each first side flap) comprises the soft, stretchable and liquid-resistant strip folded back along its transversely intermediate line with the fold defining the outer edge of this side flap, so there is no apprehension that the outer edge might irritate the wearer's skin. Such side flap can be effectively employed also for the other various wearing articles or garments including disposable diapers, training pants, incontinent pants and absorbent pads.

The other important feature of the invention such that the side flaps are formed by bonding said strips with a longitudinal tension to the basic body facilitates the pad as well as the garment to be maintained in close contact with the wearer's crotch, since they are appropriately curved under the effect of the side flaps' contraction occurring as they worn.

What is claimed is:

1. A disposable sanitary napkin capable of placement within a garment, comprising:

a liquid-permeable topsheet;

a liquid-impermeable backsheet;

a liquid-absorbent core disposed between said topsheet and backsheet;

a pair of side flaps formed separate from the topsheet and backsheet and extending along transversely opposite side edges of said core, wherein the side flaps are attached to the topsheet and the backsheet; and each of said side flaps comprising a longitudinally extending strip of soft, stretchable and liquid resistant sheet material bonded to an upper surface of said topsheet along a first side of said strip and which first side includes an intermediate portion and a free edge portion both of which portions extend inwardly from an associated side edge of the core to overlap the core when the napkin is in a flat position, each side flap including a folded portion formed outward from said side edge of said core and including a second side of said strip extending back inward from the folded portion into bonded attachment with said backsheet.

2. A disposable absorbent article according to claim 1, wherein bonding of said strips to the article is performed in a stretched condition of said strips along said side edges of said core.

3. A disposable absorbent article according to claim 1, wherein a second side flap is formed with a portion of each of said side flaps extending upward of said core to thereby define a pocket in cooperation with said topsheet.

4. A disposable absorbent article comprising:

a liquid-permeable topsheet;

a liquid-impermeable backsheet;

a liquid-absorbent core disposed between said topsheet and backsheet;

a pair of side flaps formed separate from the topsheet and backsheet and extending along transversely opposite side edges of said core, wherein the side flaps are attached to the topsheet and the backsheet; and each of said side flaps comprising a longitudinally extending strip of soft, stretchable and liquid resistant sheet material bonded to an upper surface of said topsheet along a first side of said strip and which first side extends inwardly from an associated side edge of the core to overlap the core when the article is in a flat position, each side flap including a folded portion formed outward from said side edge of said core and including a second side of said strip extending back inward from the folded portion into bonded attachment with said backsheet, wherein mutually opposed inner surfaces of each said side flap extending outward from said core are bonded to each other along a longitudinal welding line, inward from an outer side edge of said side flap, to thereby define a tunnel communicating air therethrough between said welding line and said outer side edge.

5. A disposable sanitary napkin capable of placement within a garment, comprising:

a liquid-permeable topsheet;

a liquid-impermeable backsheet;

a liquid-absorbent core disposed between said topsheet and backsheet;

a pair of side flaps formed separate from the topsheet and backsheet and extending along transversely opposite side edges of said core when the napkin is in a flat position, wherein the side flaps are attached to the topsheet and the backsheet; and each of said side flaps comprising a longitudinally extending strip of soft, stretchable and liquid resistant sheet material bonded to an upper surface of said topsheet along a first side of said strip and which first side includes an intermediate portion and a free edge portion both of which portions extend inwardly from an associated side edge of the core so that at least the free edge portion is structured to overlap the core when the napkin is in a flat position, each side flap including a folded portion formed outward from said side edge of said core and including a second side of said strip extending back inward from the folded portion into bonded attachment with said backsheet.

\* \* \* \* \*